United States Patent
Nakagawa et al.

(10) Patent No.: US 10,905,694 B2
(45) Date of Patent: Feb. 2, 2021

(54) PHARMACEUTICAL SOLID PREPARATION COMPRISING BENZAZEPINES AND PRODUCTION METHOD THEREOF

(75) Inventors: Shinsuke Nakagawa, Osaka (JP); Kai Suzuki, Osaka (JP); Tadashi Mukai, Osaka (JP)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 656 days.

(21) Appl. No.: 12/665,642

(22) PCT Filed: Jun. 20, 2008

(86) PCT No.: PCT/JP2008/061686
§ 371 (c)(1),
(2), (4) Date: Dec. 18, 2009

(87) PCT Pub. No.: WO2008/156217
PCT Pub. Date: Dec. 24, 2008

(65) Prior Publication Data
US 2010/0323006 A1    Dec. 23, 2010

(30) Foreign Application Priority Data
Jun. 21, 2007  (JP) ................. 2007-163551

(51) Int. Cl.
*A61K 31/55* (2006.01)
*A61K 9/20* (2006.01)
*A61K 9/16* (2006.01)

(52) U.S. Cl.
CPC ............ *A61K 31/55* (2013.01); *A61K 9/2027* (2013.01); *A61K 9/2054* (2013.01); *A61K 9/2059* (2013.01); *A61K 9/1623* (2013.01); *A61K 9/1652* (2013.01)

(58) Field of Classification Search
CPC .... A61K 31/55; A61K 9/2027; A61K 9/2054; A61K 9/2866
See application file for complete search history.

(56) References Cited

U.S. PATENT DOCUMENTS 2,071,511 A * 2/1937 Eldred ................ A61K 9/282
424/476
6,036,975 A   3/2000 Gebhard-Hansen et al.
6,143,323 A * 11/2000 Yabuki ................. A61K 9/2054
424/464
6,328,994 B1 * 12/2001 Shimizu et al. ............ 424/489
2002/0155156 A1 * 10/2002 Mulye ................. A61K 9/2826
424/482
2003/0236398 A1 * 12/2003 Niinobe .................. C08B 11/20
536/85
2005/0187210 A1   8/2005 Ozaki et al.
2006/0029663 A1   2/2006 Uchida et al.
2007/0071811 A1   3/2007 Kadosh et al.

FOREIGN PATENT DOCUMENTS

| EP | 1054019 A1 * | 11/2000 | ............ C08B 11/08 |
| JP | 04-154765 A | 5/1992 | |
| JP | 9-278656 A | 10/1997 | |
| JP | 11-021241 A | 1/1999 | |
| JP | 2004-137272 A | 5/2004 | |
| WO | 97/22340 A | 6/1997 | |
| WO | WO 2004073716 * | 9/2004 | |
| WO | 2005/007167 A1 | 10/2005 | |

OTHER PUBLICATIONS

Nakagawa et al. JP-11021241. "Solid Preparation Composition". Jan. 26, 1997. Machine translation.*
Shin Etsu ("L-HPC: Low-substituted hydroxypropylcellulose." http://www.metolose.jp/en/pharmaceutical/l-hpc.html. 2pgs. Aug. 20, 2019) (Year: 2019).*
Board Opinion dated Jan. 15, 2014, for CN Patent Application No. 200880021079.9.
R.C. Rowe et al., "Handbook of Pharmaceutical Excipients," Jan. 2005 (101), pp. 340.
Tu Xide, et al., Pharmacy, 3rd edition, pp. 692-693.
Gissinger et al., "A Comparative Evaluation of the Properties of Some Tablet Disintegrants," Drug Development and Industrial Pharmacy, 1980, vol. 6, No. 5, pp. 511-536 (26 pages total).

* cited by examiner

Primary Examiner — Jeffrey S Lundgren
Assistant Examiner — Chris E Simmons
(74) Attorney, Agent, or Firm — Sughrue Mion, PLLC

(57) ABSTRACT

The subject invention provides a novel pharmaceutical solid preparation that has superior disintegration properties and excellent solubility, leading to sufficient absorbability of active ingredients through the gastrointestinal tract. The pharmaceutical solid preparation of the present invention comprises:
(a) 7-chloro-5-hydroxy-1-[2-methyl-4-(2-methylbenzoylamino)benzoyl]-2,3,4,5-tetrahydro-1H-benzoazepine and/or salt thereof;
(b) hydroxypropylcellulose containing a hydroxypropoxyl group in an amount of 50% or greater; and
(c) at least one member selected from the group consisting of carmellose, sodium carboxy methyl starch, crospovidone, and low substituted hydroxypropylcellulose with an average particle diameter of 30 to 70 μm, and a 90% cumulative particle diameter of 100 to 200 μm.

6 Claims, No Drawings

PHARMACEUTICAL SOLID PREPARATION COMPRISING BENZAZEPINES AND PRODUCTION METHOD THEREOF

TECHNICAL FIELD

The present invention relates to a pharmaceutical solid preparation and a production method thereof.

BACKGROUND ART

As disclosed in Japanese Unexamined Patent Publication No. 1992-154765, 7-chloro-5-hydroxy-1-[2-methyl-4-(2-methylbenzoylamino)benzoyl]-2,3,4,5-tetrahydro-1H-benzoazepine or a salt thereof (hereinafter occasionally referred to as a benzoazepine compound) represented by General Formula (1) is useful as a vasopressin antagonist.

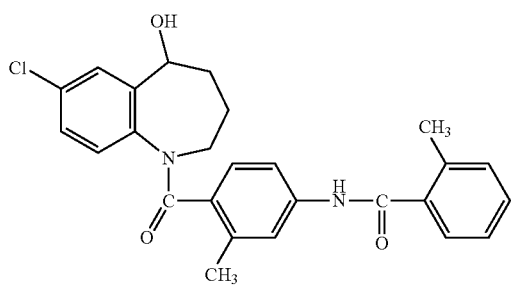

(1)

However, though a benzoazepine compound has excellent pharmacological activity, its poor solubility leads to problematic insufficient absorbability in the gastrointestinal tract.

To solve this problem, Japanese Unexamined Patent Publication No. 1999-21241 teaches a technique to improve the solubility of benzoazepine compound by combining a benzoazepine compound with a hydroxypropylcellulose, forming an amorphous composite. This technique improves the solubility of the benzoazepine compound; however, when the amorphous composite containing the benzoazepine compound is compressed directly into a tablet, the tablet does not disintegrate at all in the gastrointestinal tract. For this reason, the medicine exhibits no pharmacological activity.

The amorphous composite thus varies in disintegration properties, particularly in tablet form, and greatly varies in disintegration rate. This results in inconsistent pharmacological activity, and it is not possible to obtain medicinal products of consistent pharmacological activity.

DISCLOSURE OF THE INVENTION

An object of the present invention is to provide a novel pharmaceutical solid preparation with superior disintegration properties and excellent solubility and absorbability of active ingredients in the gastrointestinal tract. The present invention also provides a production method for the pharmaceutical solid preparation.

As a result of intensive study to solve the foregoing problems, the inventors of the present invention found that mixing an amorphous composite, obtained by a benzoazepine compound and hydroxypropylcellulose, with a specific low substituted hydroxypropylcellulose, produces a pharmaceutical solid preparation that has superior disintegration properties and excellent solubility, leading to sufficient absorbability of active ingredients in the gastrointestinal tract.

The inventors also found that mixing the amorphous composite, obtained by a benzoazepine compound and hydroxypropylcellulose, either with carmellose, sodium carboxy methyl starch or crospovidone, produces a similar pharmaceutical solid preparation.

The present invention is made in view of such findings, and provides a pharmaceutical solid preparation and a production method thereof, as defined in the following Items 1 to 30.

Item 1: A pharmaceutical solid preparation comprising:
   (a) 7-chloro-5-hydroxy-1-[2-methyl-4-(2-methylbenzoylamino)benzoyl]-2,3,4,5-tetrahydro-1H-benzoazepine and/or salt thereof;
   (b) hydroxypropylcellulose containing a hydroxypropoxyl group in an amount of 50% or greater; and
   (c) at least one member selected from the group consisting of carmellose, sodium carboxy methyl starch, crospovidone, and low substituted hydroxypropylcellulose with an average particle diameter of 30 to 70 μm, and a 90% cumulative particle diameter of 100 to 200 μm.

Item 2: A pharmaceutical solid preparation comprising:
   (a) 7-chloro-5-hydroxy-1-[2-methyl-4-(2-methylbenzoylamino)benzoyl]-2,3,4,5-tetrahydro-1H-benzoazepine and/or salt thereof;
   (b) hydroxypropylcellulose containing a hydroxypropoxyl group in an amount of 50% or greater; and
   (c-1) low substituted hydroxypropylcellulose, an average particle diameter of 30 to 70 μm, and a 90% cumulative particle diameter of 100 to 200 μm.

(This pharmaceutical solid preparation is referred to as a "Solid Preparation A", hereinafter)

Item 3: The pharmaceutical solid preparation according to Item 2, wherein the low substituted hydroxypropylcellulose has an average particle diameter 45 to 65 μm, and a 90% cumulative particle diameter of 100 to 200 μm.

Item 4: The pharmaceutical solid preparation according to Item 2, wherein the low substituted hydroxypropylcellulose has an average particle diameter of 45 to 65 μm, and a 90% cumulative particle diameter of 150 to 200 μm.

Item 5: The pharmaceutical solid preparation according to any one of Items 2 to 4, wherein the pharmaceutical solid preparation is a form of tablet.

Item 6: The pharmaceutical solid preparation according to claim 2, obtained by a method, comprising:

Step 1 of producing an amorphous composite from 7-chloro-5-hydroxy-1-[2-methyl-4-(2-methylbenzoylamino)benzoyl]-2,3,4,5-tetrahydro-1H-benzoazepine and/or a salt thereof, and hydroxypropylcellulose containing a hydroxypropoxyl group in an amount of 50% or greater;

Step 2 of mixing the amorphous composite obtained in Step 1 with low substituted hydroxypropylcellulose, an average particle diameter of 30 to 70 μm, and a 90% cumulative particle diameter of 100 to 200 μm; and Step 3 of processing the mixture obtained in Step 2 into a solid preparation.

Item 7: The pharmaceutical solid preparation according to Item 6, produced by a method further comprising, between Step 1 and Step 2, the step of processing the amorphous composite obtained in Step 1 into granules using a granulation method.

Item 8: The pharmaceutical solid preparation according to Item 6, produced by a method further comprising, between Step 2 and Step 3, the step of processing the mixture obtained in Step 2 into granules using a granulation method.

Item 9: A method for producing the pharmaceutical solid preparation according to Item 2, the method comprising:

Step 1 of producing an amorphous composite from 7-chloro-5-hydroxy-1-[2-methyl-4-(2-methylbenzoylamino)benzoyl]-2,3,4,5-tetrahydro-1H-benzoazepine and/or a salt thereof, and hydroxypropylcellulose containing a hydroxypropoxyl group in an amount of 50% or greater;

Step 2 of mixing the amorphous composite obtained in Step 1 with low substituted hydroxypropylcellulose, an average particle diameter of 30 to 70 μm, and a 90% cumulative particle diameter of 100 to 200 μm; and Step 3 of processing the mixture obtained in Step 2 into a solid preparation.

Item 10: The method according to Item 9, wherein Step 3 is carried out by processing the mixture obtained in Step 2 into tablets.

Item 11: The method according to Item 9 or 10, further comprising, between Step 1 and Step 2, the step of processing the amorphous composite obtained in Step 1 into granules using a granulation method.

Item 12: The method according to Item 9 or 10, further comprising, between Step 2 and Step 3, the step of processing the mixture obtained in Step 2 into granules using a granulation method.

Item 13: A pharmaceutical solid preparation comprising:
  (a) 7-chloro-5-hydroxy-1-[2-methyl-4-(2-methyl benzoylamino)benzoyl]-2,3,4,5-tetrahydro-1H-benzoazepine and/or a salt thereof;
  (b) hydroxypropylcellulose containing a hydroxy propoxyl group in an amount of 50% or greater; and
  (c-2) carmellose.

(This pharmaceutical solid preparation is referred to as a "Solid Preparation B", hereinafter)

Item 14: The pharmaceutical solid preparation according to Item 13, wherein the content of the carmellose is 7 to 15 wt. %, based on the total quantity of the pharmaceutical solid preparation.

Item 15: A method for producing the pharmaceutical solid preparation according to Item 13, the method comprising:

Step 1 of producing an amorphous composite from 7-chloro-5-hydroxy-1-[2-methyl-4-(2-methylbenzoylamino)benzoyl]-2,3,4,5-tetrahydro-1H-benzoazepine and/or a salt thereof, and hydroxypropylcellulose containing a hydroxypropoxyl group in an amount of 50% or greater;

Step 2 of mixing the amorphous composite obtained in Step 1 with carmellose; and Step 3 of processing the mixture obtained in Step 2 into a solid preparation.

Item 16: The method according to Item 15, wherein Step 3 is carried out by processing the mixture obtained in Step 2 into tablets.

Item 17: The method according to Item 15 or 16, further comprising, between Step 1 and Step 2, the step of processing the amorphous composite obtained in Step 1 into granules using a granulation method.

Item 18: The method according to Item 15 or 16, further comprising, between Step 2 and Step 3, the step of processing the mixture obtained in Step 2 into granules using a granulation method.

Item 19: A pharmaceutical solid preparation comprising:
  (a) 7-chloro-5-hydroxy-1-[2-methyl-4-(2-methylbenzoylamino)benzoyl]-2,3,4,5-tetrahydro-1H-benzoazepine and/or a salt thereof;
  (b) hydroxypropylcellulose containing a hydroxypropoxyl group in an amount of 50% or greater; and
  (c-3) sodium carboxy methyl starch.

(This pharmaceutical solid preparation is referred to as a "Solid Preparation C", hereinafter)

Item 20: The pharmaceutical solid preparation according to claim 19, wherein the content of the sodium carboxy methyl starch is 0.5 to 15 wt. %, based on the total quantity of the pharmaceutical solid preparation.

Item 21: A method for producing the pharmaceutical solid preparation according to Item 19, the method comprising:

Step 1 of producing an amorphous composite from 7-chloro-5-hydroxy-1-[2-methyl-4-(2-methylbenzoylamino)benzoyl]-2,3,4,5-tetrahydro-1H-benzoazepine and/or a salt thereof, and hydroxypropylcellulose containing a hydroxypropoxyl group in an amount of 50% or greater;

Step 2 of mixing the amorphous composite obtained in Step 1 with sodium carboxy methyl starch; and Step 3 of processing the mixture obtained in Step 2 into a solid preparation.

Item 22: The method according to Item 21, wherein Step 3 is carried out by processing the mixture obtained in Step 2 into tablets.

Item 23: The method according to Item 21 or 22, further comprising, between Step 1 and Step 2, the step of processing the amorphous composite obtained in Step 1 into granules using a granulation method.

Item 24: The method according to Item 21 or 22, further comprising, between Step 2 and Step 3, the step of processing the mixture obtained in Step 2 into granules using a granulation method.

Item 25: A pharmaceutical solid preparation comprising:
  (a) 7-chloro-5-hydroxy-1-[2-methyl-4-(2-methylbenzoylamino)benzoyl]-2,3,4,5-tetrahydro-1H-benzoazepine and/or a salt thereof;
  (b) hydroxypropylcellulose containing a hydroxypropoxyl group in an amount of 50% or greater; and
  (c-4) crospovidone.

(This pharmaceutical solid preparation is referred to as a "Solid Preparation D", hereinafter)

Item 26: The pharmaceutical solid preparation according to Item 25, wherein the content of the crospovidone is 2 to 15 wt. %, based on the total quantity of the pharmaceutical solid preparation.

Item 27: A method for producing the pharmaceutical solid preparation according to Item 25, the method comprising:

Step 1 of producing an amorphous composite from 7-chloro-5-hydroxy-1-[2-methyl-4-(2-methylbenzoylamino)benzoyl]-2,3,4,5-tetrahydro-1H-benzoazepine and/or a salt thereof, and hydroxypropylcellulose containing a hydroxypropoxyl group in an amount of 50% or greater;

Step 2 of mixing the amorphous composite obtained in Step 1 with crospovidone; and Step 3 of processing the mixture obtained in Step 2 into a solid preparation.

Item 28: The method according to Item 27, wherein Step 3 is carried out by processing the mixture obtained in Step 2 into tablets.

Item 29: The method according to Item 27 or 28, further comprising, between Step 1 and Step 2, the step of processing the amorphous composite obtained in Step 1 into granules using a granulation method.

Item 30: The method according to Item 27 or 28, further comprising, between Step 2 and Step 3, the step of processing the mixture obtained in Step 2 into granules using a granulation method.

A pharmaceutical solid preparation according to the present invention comprises:
  (a) 7-chloro-5-hydroxy-1-[2-methyl-4-(2-methylbenzoylamino)benzoyl]-2,3,4,5-tetrahydro-1H-benzoazepine and/or salt thereof;

(b) hydroxypropylcellulose containing a hydroxypropoxyl group in an amount of 50% or greater; and
(c) at least one member selected from the group consisting of carmellose, sodium carboxy methyl starch, crospovidone, and low substituted hydroxypropylcellulose with an average particle diameter of 30 to 70 μm, and a 90% cumulative particle diameter of 100 to 200 μm.

In the present invention, a solid preparation containing, as the component (c) low substituted hydroxypropylcellulose, an average particle diameter of 30 to 70 μm, and a 90% cumulative particle diameter of 100 to 200 μm is referred to as a Solid Preparation A; a solid preparation containing carmellose as the essential ingredient of component (c) is referred to as Solid Preparation B; a solid preparation containing sodium carboxy methyl starch as the essential ingredient of component (c) is referred to as Solid Preparation C; and a solid preparation containing crospovidone as the essential ingredient of Component (c) is referred to as Solid Preparation D.

The following explains Solid Preparation A, Solid Preparation B, Solid Preparation C, and Solid Preparation D, in that order.

Solid Preparation A

As described above, Solid Preparation A of the present invention comprises:
(a) 7-chloro-5-hydroxy-1-[2-methyl-4-(2-methylbenzoylamino)benzoyl]-2,3,4,5-tetrahydro-1H-benzoazepine and/or a salt thereof (benzoazepine compound),
(b) hydroxypropylcellulose containing a hydroxypropoxyl group in an amount of 50% or greater, and
(c-1) low substituted hydroxypropylcellulose, an average particle diameter of 30 to 70 μm, and a 90% cumulative particle diameter of 100 to 200 μm.

(a) Benzoazepine Compound

The benzoazepine compound is 7-chloro-5-hydroxy-1-[2-methyl-4-(2-methylbenzoylamino)benzoyl]-2,3,4,5-tetrahydro-1H-benzoazepine and/or a salt thereof represented by the following General Formula (1).

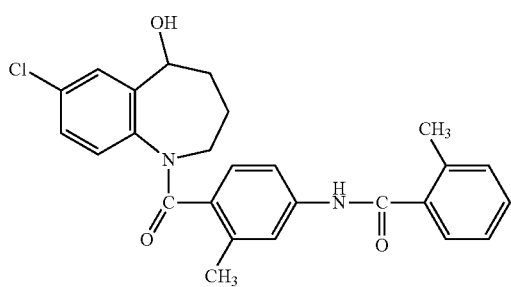

(1)

The salt of benzoazepine designates, for example, salt obtained by mixing an acid or a basic compound pharmacologically compatible with the benzoazepine represented by General Formula (1).

Examples of the basic compound which forms salt with benzoazepine include metal hydroxides such as sodium hydroxides, potassium hydroxides, lithium hydroxides, calcium hydroxides; alkali metal carbonates such as sodium carbonates; alkali metal bicarbonates such as sodium hydrogen carbonates; and alkali metal alcoholates such as sodium methylates or potassium ethylates.

Examples of the acid which forms salt with benzoazepine include inorganic acids such as sulfuric acid, nitric acid, hydrochloric acid, or hydrobromic acid; and organic acids such as acetic acid, p-toluene sulfonic acid, ethane sulfonic acid, oxalic acid, maleic acid, fumaric acid, citric acid, succinic acid, or benzoic acid.

Examples of the benzoazepine compound include solvates of benzoazepine such as hydrates and ethanolates.

The Component (a) as the benzoazepine compound may be selected from various crystal polymorphisms. Additionally, there are various stereoisomers and opticalisomers of the benzoazepine compound of the present invention. It is also possible to use them as Component (a).

These various substances used as the benzoazepine compound of the present invention may be used solely or in combination. More specifically, the benzoazepine compound of the present invention comprises at least one member selected from the group consisting of 7-chloro-5-hydroxy-1-[2-methyl-4-(2-methylbenzoylamino)benzoyl]-2,3,4,5-tetrahydro-1H-benzoazepine and salt thereof.

The benzoazepine compound of the present invention may be produced with any publicly known method, for example, the method disclosed in Japanese Unexamined Patent Publication No. 1992-154765 or No. 1999-21241.

(b) Hydroxypropylcellulose

Component (b) is water-soluble cellulose ether containing a hydroxyl propyl group in an amount of about 50% or greater, preferably in a range from about 53 to 80 wt. %. Component (b) is a compound having a repeating unit represented by the following General Formula (2).

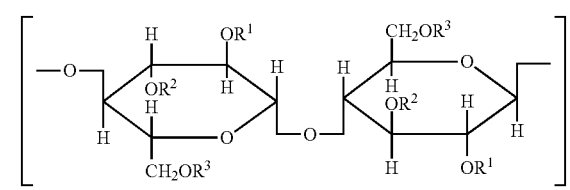

wherein $R^1$, $R^2$ and $R^3$ each represents a hydrogen atom or a group:

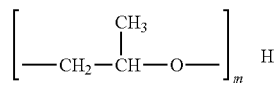

(m is an integer not less than 1).

The hydroxypropylcellulose containing a hydroxypropoxyl group in an amount of 50% or greater can be any compound represented by the foregoing Formula (2). However, in the case of 2% aqueous solution, the viscosity of the aqueous solution is preferably 2 to 10 cps, and more preferably 3 to 6 cps at 20° C.

The hydroxypropylcellulose containing a hydroxypropoxyl group in an amount of 50% or greater used for the present invention can be produced by a publicly known method, or may be selected from commercially available products. Examples of the marketed commodity of the hydroxypropylcellulose containing a hydroxy propoxyl group in an amount of 50% or greater include "HPC-L", "HPC-SL", and "HPC-SSL" (Nippon Soda Co. Ltd.), and "Klucel EF" (Hercules).

(c-1) Low Substituted Hydroxypropylcellulose

The low substituted hydroxypropylcellulose is cellulose containing a hydroxy propoxyl group in an amount of about 5 to 16 wt. %, preferably in an amount of about 10 to 13 wt. %.

The average particle diameter of the low substituted hydroxypropylcellulose approximately ranges from 30 to 70 µm, preferably from 45 to 65 µm.

Further, the 90% cumulative particle diameter of the low substituted hydroxypropylcellulose is generally around 100 to 200 µm, and preferably ranges from 150 to 200 µm.

The average particle diameter and 90% cumulative particle diameter falling within the foregoing range secure the disintegration properties of the solid preparation.

The content of the low substituted hydroxypropylcellulose can be measured by a method according to Japanese Pharmacopoeia, for example.

Further, the particle distribution and the average particle diameter of the low substituted hydroxypropylcellulose may be measured by a dry method using a laser diffraction type particle size distribution analyzer. The resulting value is used to find the 90% cumulative particle diameter.

The low substituted hydroxypropylcellulose preferably has a small water-soluble content in terms of security for the disintegration property. The water soluble content is preferably about 3% or less.

The low substituted hydroxypropylcellulose used for the present invention can be produced by a publicly known method, or may be selected from commercially available products. Examples of the marketed commodity of low substituted hydroxypropylcellulose include "LH-11", "LH-21", and "LH-B1" (Shin-Etsu Chemical Co., Ltd.).

The (c-1) low substituted hydroxypropylcellulose may be used with other disintegrating agents, insofar as the effects of the present invention are not impaired. In this case, plural kinds of disintegrating agents may be used with the hydroxypropylcellulose.

Further, the (c-1) low substituted hydroxypropylcellulose is used not only as a disintegrating agent, but also as other kinds of agents, such as binders, diluents, or other additives.

The (c-1) low substituted hydroxypropylcellulose is preferable because it is compatible with the drug and also easy to handle.

The content of the (a) benzoazepine compound in Solid Preparation A is not particularly limited, and may range widely. The content is generally about 0.01 to 95 wt. %, preferably about 0.05 to 65 wt. %, and more preferably about 0.1 to 50%.

The content of the (b) hydroxypropylcellulose containing a hydroxy propoxyl group in an amount of 50% or greater is generally about 0.01 to 2 times, preferably about 0.1 to 1.5 times, and particularly preferably about 0.2 to 1 times the (a) benzoazepine compound in weight.

The content of the (c-1) low substituted hydroxypropylcellulose in Solid Preparation A is generally about 1 to 15 wt. %, preferably about 2 to 13 wt. %, and more preferably about 3 to 12 wt. %. This content range ensures desirable disintegration properties.

The (a) benzoazepine compound and the (b) hydroxypropylcellulose containing a hydroxy propoxyl group in an amount of 50% or greater are contained in Solid Preparation A in the form of an amorphous composite.

Other Ingredients

In addition to the aforementioned Components (a), (b) and (c-1), Solid Preparation A of the present invention may contain other regular ingredients for pharmaceutical solid preparations, such as diluents, binders, pH adjusters, absorption enhancers, lubricants, coloring agents, corrective substances, or perfumes. The contents of these ingredients fall within a range not to impair the effects of the present invention.

Solid Preparation A may be a form of powder, granule, tablet, pill, capsule etc.

Among these, the present invention prefers the form of a powder, granule, capsules, or tablet in view of the benefits of easy dosages. The tablet form is particularly preferable.

Production Method for Solid Preparation A

A production method for Solid Preparation A of the present invention comprises the following Steps 1, 2 and 3.

Step 1: producing an amorphous composite from 7-chloro-5-hydroxy-1-[2-methyl-4-(2-methyl benzoylamino) benzoyl]-2,3,4,5-tetrahydro-1H-benzoazepine and/or a salt thereof (benzoazepine compound), and hydroxypropylcellulose containing a hydroxy propoxyl group in an amount of 50% or greater;

Step 2: mixing the amorphous composite produced in Step 1 with low substituted hydroxypropylcellulose; and Step 3: processing the mixture obtained in Step 2 into a solid preparation.

The following details Step 1, Step 2 and Step 3.

Step 1

Step 1 is a process for producing an amorphous composite from a benzoazepine compound, and hydroxypropylcellulose containing a hydroxy propoxyl group in an amount of 50% or greater. The amorphous composite can be produced in many ways, including the following.

i) A benzoazepine compound and a hydroxypropylcellulose containing a hydroxy propoxyl group in an amount of 50% or greater are dissolved in an organic solvent, and the organic solvent is then distilled off by a known method to obtain a solid composite (e.g., a powder) of the amorphous composite.

ii) The amorphous composite can also be produced using a heat-melt kneading technology; for example, using a two-screw extruder. This method, which does not use an organic solvent, has advantages such as low environmental pollution risk and high production efficiency.

iii) The amorphous composite can also be produced using an ultrasonic tablet producing machine (rotary tablet machine, compression molding machine, etc.).

When using an organic solvent in Step 1, any conventionally-known organic solvent that can dissolve the hydroxypropylcellulose containing benzoazepine and a hydroxy propoxyl group in an amount of 50% or greater can be used. Examples of the organic solvent include lower alcohols such as methanol, ethanol or isopropanol; ketones such as acetone, methyl ethyl ketone; halogenation carbon hydrides such as dichloromethane, dichloroethane, chloroform, or carbon tetrachloride; and mixed solvents of those. Among them, a mixed solvent of lower alcohol and halogenation carbon hydride are particularly preferable in terms of solubility, distillation, etc. A mixed solvent of dichloromethane, and methanol and/or ethanol is particularly preferable.

When using a mixed solution of a lower alcohol and a halogenation carbonhydride, the lower alcohol and the halogenation carbon hydride are mixed at a weight ratio of about 99:1 to 1:99. When using a mixed solution of methanol and/or ethanol and dichloromethane, the methanol and/or ethanol and the dichloromethane are mixed at a weight ratio of about 99:1 to 1:99, preferably 10:90 to 40:60. 0.01 to 5 wt. % of water may be added to the organic solvent.

When using an organic solvent in Step 1, the organic solvent can be distilled off by an evaporation method, spray drying method, fluidized bed drying method or the like. A spray drying method is preferable.

The shape of the amorphous composite of the present invention is not particularly limited. The amorphous composite may be in the form of a powder, or a round or square solid of a certain size.

Step 2

Step 2 is a process for mixing the amorphous composite produced from Component (a) and Component (b) in Step 1 with (c-1) low substituted hydroxypropylcellulose. The mixing method is not particularly limited. For example, a diffusion blender (a container rotating type), a convection mixer (a machine stirring type), a kneader, an airflow type mixer or the like can be used.

After mixing the amorphous composite with Component (c-1), a lubricant may be added. Adding a lubricant gives some effects, including suppression of impediments in the following Step 3 of processing the solid preparation into tablets.

Examples of lubricants include powdered gum arabic, carnauba wax, carmellose calcium, carmellose sodium, hydrated silicon dioxide, dried aluminum hydroxide gel, grycerol esters of fatty acid, magnesium silicate, light anhydrous silicic acid, crystalline cellulose, hydrogenated oil, synthetic aluminum silicate, magnesium oxide, wheat starch, white beeswax, heavy anhydrous silicic acid, sucrose esters of fatty acid, stearyl alcohol, stearic acid, aluminum stearate, calcium stearate, polyoxyl 40 stearate, magnesium stearate, cetanol, gelatin, talc, magnesium carbonate, precipitated calcium carbonate, corn starch, lactose, sucrose, hard fat, potato starch, fumaric acid, sodium stearyl fumarate, polyoxyethylene (160), polyoxypropylene (30) glycol, polysorbate 80, macrogol 400, macrogol 600, macrogol 1500, macrogol 4000, macrogol 6000, yellow beeswax, magnesium aluminometasilicate, methylcellulose, glyceryl monostearate, lauryl sulfate sodium, calcium sulfate, and magnesium sulfate.

The production method of the present invention preferably comprises, between Step 1 and Step 2, Step 1' of processing the amorphous composite into granules using a granulation method, or, between Step 2 and Step 3, Step 2' of processing the mixture resulting from Step 2 into granules using a granulation method.

In the granulation method in Step 1' or in Step 2', it is preferable to use a diluent and a binder.

Examples of the diluent used in the granulation method include L-aspartic acid, maltose syrup powder, acacia, powdered acacia, alginic acid, sodium alginate, pregelatinized starch, inositol, ethylcellulose, ethylene and vinyl acetate copolymer, erythritol, sodium chloride, kaolin, casein, sodium caseinate, fructose, sodium carboxy methyl starch, carmellose, carmellose calcium, carmellose sodium, hydrated silicon dioxide, amorphous silicon oxide hydrate, agar, powdered agar, xylitol, citric acid, glycine, glycerol esters of fatty acid, crosscarmellose sodium, crospovidone, magnesium aluminosilicate, calcium silicate, magnesium silicate, light anhydrous silicic acid, crystalline cellulose, crystalline cellulose and carmellose sodium, hydrogenated oil, wheat starch, potassium acetate, calcium acetate, cellulose acetate phthalate, titanium oxide, magnesium oxide, β-cyclodextrin, heavy anhydrous silicic acid, tartaric acid, sucrose esters of fatty acid, magnesium hydroxide-aluminium hydroxide co-precipitate, magnesium hydroxide, stearyl alcohol, stearic acid, and calcium stearate, polyoxyl stearate 40, magnesium stearate, purification gelatin, purified shellac, purified urea, sucrose, sorbitan sesquioleate, cetanol, cetostearyl alcohol, gelatin, D-sorbitol, tribasic calcium phosphate, soybean hydrogenated oil, soybean lecithin, talc, ammonium carbonate, calcium carbonate, magnesium carbonate, low substituted sodium carboxy methyl starch, low substituted hydroxypropylcellulose, dextrin, corn starch, silicon dioxide, aluminum lactate, calcium lactate, lactose monohydrate, white shellac, white soft sugar, potato starch, crystallite cellulose, hydroxypropyl starch, hydroxypropylcellulose, hypromellose 2208, hypromellose 2906, hypromellose 2910, hypromellose phthalate, partly pregelatinized starch, pullulan, powdered sucrose, powdered hydrogenated maltose starch syrup, pectin, povidone, polyoxy ethylene hydrogenated castor oil 60, sodium polystyrene sulfonate, polysorbate 80, macrogol 400, macrogol 1500, macrogol 4000, macrogol 6000, maltitol, maltose, maltose monohydrate, D-mannitol, starch syrup, anhydrous citric acid, anhydrous silicic acid hydrate, anhydrous lactose, anhydrous sodium sulfate, anhydrous dibasic calcium phosphate, methacrylic acid copolymer LD, magnesium aluminometasilicate, methylacrylate methacrylic acid copolymer, methylcellulose, aluminum monostearate, glycerin monostearate, sorbitan monostearate, lauryl sulfate sodium, aluminum sulfate, calcium sulfate, DL-malic acid, calcium monohydrogen phosphate, dibasic calcium phosphate, dibasic sodium phosphate, dibasic potassium phosphate, monobasic calcium phosphate, and sodium dihydrogen phosphate dihydrate.

Examples of the binder include ethyl acrylate and methyl methacrylate copolymer dispersion, aminoalkyl methacrylate copolymer E, aminoalkyl methacrylate copolymer RS, amylopectin, maltose syrup powder, acacia, powdered acacia, sodium alginate, pregelatinized starch, ethylcellulose, powdered hydrolyzed gelatin, sodium caseinate, fructose, carboxy vinyl polymer, carboxymethyl ethylcellulose, sodium carboxymethyl starch, carmellose, carmellose sodium, hydrated silicon dioxide, agar, hydrogenated tallow, powdered agar, guar Gum, glycerin, light anhydrous silicic acid, crystalline cellulose, hydrogenated oil, synthetic aluminum silicate, poly [(2-oxo-1pyrrolidinyl) ethylene], copolyvidone, rice powder, wheat starch, polyvinyl acetate, cellulose acetate phthalate, white beeswax, sucrose esters of fatty acid, stearyl alcohol, stearic acid, calcium stearate, polyoxyl 40 stearate, purified gelatin, purified shellac, sucrose, sorbitan sesquioleate, cetanol, shellac, sorbitan esters of fatty acid, D-sorbitol, soybean lecithin, calcium carbonate, low substituted hydroxypropylcellulose, dextrin, starch, corn starch, tragacanth, powdered tragacanth, lactose monohydrate, concentrated glycerin, white shellac, potato starch, microcrystallite cellulose, hydroxyethylcellulose, hydroxyethylmethylcellulose, hydroxypropylcellulose, hypromellose 2208, hypromellose 2906, hypromellose 2910, hydroxypropylmethylcellulose acetate succinate, hypromellose phthalate, vinylpyrrolidone and vinyl acetate copolymer, glucose, partly pregelatinized starch, mixture of fumaric acid, fumaric acid and stearic acid and polyvinyl acetal diethylamino acetate, and hydroxypropyl methylcellulose 2910, pullulan, propylene glycol, pectin, povidone, polyoxy ethylene (160) polyoxy propylene (30) glycol, polysorbate 80, polyvinyl acetal diethyl amino acetate, fully hydrolyzed polyvinyl alcohol, partially hydrolyzed polyvinyl alcohol, sodium polyphosphate, macrogol 400, macrogol 1500, macrogol 4000, macrogol 6000, D-mannitol, starch syrup, yellow beeswax, methacrylic acid copolymer L, methacrylic acid copolymer LD, methacrylic acid copolymer S, magnesium aluminometasilicate, sodium metaphosphate, methylcellulose, glyceryl monostearate, and lauryl sulfate sodium.

In the production method according to the present invention, by performing Step 1' after Step 1, or Step 2' after Step 2, it is possible to improve the content uniformity of component (a) in the solid preparations that contains a low proportion of Component (a). Further, filling a solid preparation into dies of tabletting machine is improved because the solid preparation is densified in a granulation process. The granulation method in Step 1' or 2' is not particularly limited, and any granulation method may be used according to, for example, the target dosage forms. Examples of the granulation methods include dry granulation methods and wet granulation methods (e.g., a fluidized-bed granulation method, a kneading granulation method, etc.).

Step 3

Step 3 is a step for processing the mixture obtained in Step 2 into a solid preparation.

The method for processing the mixture into a solid preparation depends on the target dosage forms. For example, when the target dosage form of a solid preparation is tablets, the mixture may be compressed with a tabletting machine. Examples of the tabletting methods include dry tabletting method, a wet tabletting method, and an external lubrication tabletting method, etc.

Further, the solid preparation may be film-coated to mask the drug related taste, or to improve the photostability. Solid Preparation A may be coated with an enteric film or a sustained-release film to modify a drug release in the gastrointestinal tract.

Solid Preparation B

Solid Preparation B of the present invention contains:
(a) 7-chloro-5-hydroxy-1-[2-methyl-4-(2-methyl benzoylamino)benzoyl]-2,3,4,5-tetrahydro-1H-benzoazepine and/or a salt thereof;
(b) hydroxypropylcellulose containing a hydroxy propoxyl group in an amount of 50% or greater; and
(c-2) Carmellose.

The following details each of Components (a), (b) and (c-2).

(a) Benzoazepine Compound

Solid Preparation B uses the same benzoazepine compound as Solid Preparation A.

(b) Hydroxypropylcellulose

The hydroxypropylcellulose used for Solid Preparation B is the same hydroxypropylcellulose containing a hydroxy propoxyl group in an amount of 50% or greater used for Solid Preparation A.

(c-2) Carmellose

Carmellose can be produced with one of the publicly known methods. Additionally, commercial items such as the "NS-300", produced by Nichirin Chemical Co., are readily available.

Solid Preparation B may contain other disintegrating agents together with the (c-2) carmellose within a range not to impair the effect of the present invention. In this case, plural kinds of disintegrating agents may be used.

The (c-2) carmellose is used not only as a disintegrating agent, but also as a binder, a diluent, or other additive.

The content of the (a) benzoazepine compound in the solid formulation B is not particularly limited and can vary widely, but is generally about 0.01 to 95 wt. %, preferably about 0.05 to 65 wt. %, and more preferably 0.1 to 50%.

The proportion of the (b) hydroxypropylcellulose containing at least 50% hydroxy propoxyl group is generally 0.01 to 2 times, preferably 0.1 to 1.5 times, and particularly preferably 0.2 to 1 times the (a) benzoazepine compound.

The content of the (c-2) carmellose in Solid Preparation B is generally 7 to 15 wt. %, preferably 9 to 13 wt. %, and more preferably 10 to 12 wt. %. The content in this range ensures a desirable disintegration property.

In Solid Preparation B, each of the (a) benzoazepine compound and the (b) hydroxypropylcellulose containing a hydroxy propoxyl group in an amount of 50% or greater is a form of amorphous composite.

Other Ingredient

As with Solid Preparation A, Solid Preparation B may contain other ingredients for use in pharmaceutical solid preparations, in addition to the Components (a), (b) and (c-2).

Examples of the ingredients include diluents, binders, pH adjusters, absorption enhancers, lubricants, colorant flavoring agents, or perfumes.

The contents of these additional ingredients fall within the range not to impair the effect of the present invention.

As with Solid Preparation A, Solid Preparation B containing (a) benzoazepine compound, the (b) hydroxypropylcellulose containing a hydroxy propoxyl group in an amount of 50% or greater, and the (c-2) carmellose may be a form of powder, granule, tablet, pill, or capsule. Among these, the present invention prefers the form of a powder, granule, capsules, and tablet in view of easy preparation and dose. The tablet form is particularly preferable.

Production Method for Solid Preparation B

Solid Preparation B is prepared in the same manner as Solid Preparation A, except that carmellose is used instead of the low substituted hydroxypropylcellulose.

Solid Preparation C

Solid Preparation C of the present invention comprises:
(a) 7-chloro-5-hydroxy-1-[2-methyl-4-(2-methyl benzoylamino)benzoyl]-2,3,4,5-tetrahydro-1H-benzoazepine and/or a salt thereof;
(b) hydroxypropylcellulose containing a hydroxy propoxyl group in an amount of 50% or greater; and
(c-3) sodium carboxy methyl starch.

The following details each of Components (a), (b) and (c-3).

(a) Benzoazepine Compound

Solid Preparation C uses the same benzoazepine compound as Solid Preparation A.

(b) Hydroxypropylcellulose

The hydroxypropylcellulose used for Solid Preparation C is the same as the hydroxypropylcellulose containing a hydroxy propoxyl group in an amount of 50% or greater used for Solid Preparation A.

(c-3) Sodium Carboxy Methyl Starch

Sodium carboxy methyl starch can be obtained easily from commercial items, for example, "GLYCOLYS LV" (Roquette), and "Primojel" (DMV). Partly pregelatinized starch may also be used as Component (c-3).

The partly pregelatinized starch can be obtained easily from commercial items, for example, "PCS" (Asahi Kasei Chemicals), "Starch 1500" (Colorcon), or "LYCATAB C" (Roquette).

The average particle diameter of the sodium carboxy methyl starch is, for example, not more than 105 μm, preferably not more than 80 μm, and more preferably about 20 to 65 μm.

The average particle diameter of the partly pregelatinized starch is, for example, not more than 150 μm, preferably not more than 100 μm, and more preferably about 15 to 85 μm.

Further, the water soluble content of the partly pregelatinized starch is generally about not more than 20 wt. %, preferably about not more than 10 wt. %, and further preferably about 1 to 4 wt. %, with respect to room-temperature water.

In addition, metal-free partly pregelatinized starch or the like also exhibits a relatively desirable disintegration property when used in a small amount as the disintegrating agent in the solid preparation. The metal-free partly pregelatinized starch can therefore be useful for the solid preparation of the present invention when the content of the disintegrating agent is small.

As the content of the disintegrating agent increases, metal-containing sodium carboxy methyl starch becomes more suitable than metal-free partly pregelatinized starch, in terms of disintegration properties.

In contrast, in the cellulose disintegrating agent such as the foregoing (c-1) low substituted hydroxypropylcellulose or (c-2) carmellose, a metal-free substance is more suitable than a metal-containing substance, in terms of disintegration properties, regardless of its content.

Solid Preparation C may contain other disintegrating agents together with the (c-3) sodium carboxy methyl starch within a range not to impair the effect of the present invention. In this case, plural kinds of disintegrating agents may be used.

The (c-3) sodium carboxy methyl starch is used not only as a disintegrating agent, but also as a binder, a diluent, or another additive.

The content of the (a) benzoazepine compound in the solid formulation B is not particularly limited and can vary widely, but is generally about 0.01 to 95 wt. %, preferably about 0.05 to 65 wt. %, and more preferably 0.1 to 50%.

The proportion of the (b) hydroxypropylcellulose containing at least 50% hydroxy propoxyl group is generally about 0.01 to 2 times, preferably about 0.1 to 1.5 times, and particularly preferably about 0.2 to 1 times the (a) benzoazepine compound.

The content of the (c-3) sodium carboxy methyl starch in Solid Preparation C is generally about 0.5 to 15 wt. %, preferably about 1 to 10 wt. %, and more preferably about 1 to 5 wt. %. The content in this range ensures desirable disintegration properties.

When using partly pregelatinized starch as Component (c-3), the content is not particularly limited; however, the content is generally about 1 to 15 wt. %, preferably about 2 to 10 wt. %, and more preferably about 3 to 7 wt. %, based on the whole quantity of the solid preparation.

Other Ingredient

As with Solid Preparation A, Solid Preparation C may contain other ingredients for use in pharmaceutical solid preparations in addition to the Components (a), (b) and (c-3). Examples of the ingredients include diluents, binders, pH adjusters, absorption enhancers, lubricants, colorant flavoring agents or perfumes.

The contents of these additional ingredients fall within the range not to impair the effect of the present invention.

As with Solid Preparation A, Solid Preparation C containing (a) benzoazepine compound, the (b) hydroxypropylcellulose containing a hydroxy propoxyl group in an amount of 50% or greater, and the (c-3) sodium carboxy methyl starch may be in the form of a powder, granule, tablet, pill, or capsule. Among these, the present invention prefers powders, granules, capsules, and tablets, in view of easy preparation and dose. Tablets are particularly preferable.

Production Method for Solid Preparation C

Solid Preparation C is prepared in the same manner as Solid Preparation A, except that sodium carboxy methyl starch is used instead of low substituted hydroxypropylcellulose.

Solid Preparation D

Solid Preparation D according to the present invention comprises:

(a) 7-chloro-5-hydroxy-1-[2-methyl-4-(2-methyl benzoylamino)benzoyl]-2,3,4,5-tetrahydro-1H-benzoazepine and/or salt thereof;

(b) hydroxypropylcellulose containing a hydroxy propoxyl group in an amount of 50% or greater; and (c-4) crospovidone.

The following details each of Components (a), (b) and (c-4).

(a) Benzoazepine Compound

The benzoazepine compound used for Solid Preparation D is the same as the benzoazepine compound used for Solid Preparation A.

(b) Hydroxypropylcellulose

The hydroxypropylcellulose used for Solid Preparation D is the same as the hydroxypropylcellulose containing a hydroxy propoxyl group in an amount of 50% or greater used for Solid Preparation A.

(c-4) Crospovidon

Crospovidon designates a synthetic cross-linked homopolymer of N-vinyl-2-pyrrolidinone, not soluble in water.

The content of the (a) benzoazepine compound in Solid Preparation D is not particularly limited and can vary widely, but is generally about 0.01 to 95 wt. %, preferably about 0.05 to 65 wt. %, and more preferably 0.1 to 50 wt. %.

The proportion of the (b) hydroxypropylcellulose containing at least 50% hydroxy propoxyl group is generally about 0.01 to 2 times, preferably about 0.1 to 1.5 times, and particularly preferably about 0.2 to 1 times the (a) benzoazepine compound.

The content of the (c-4) crospovidone in Solid Preparation D is generally about 2 to 15 wt. %, preferably about 3 to 12 wt. %, and more preferably about 3 to 10 wt. %. The content in this range ensures desirable disintegration properties.

Solid Preparation D may contain other disintegrating agent for use in pharmaceutical solid preparations, in addition to the (c-4) crospovidone. In this case, plural kinds of disintegrating agents may be used. The (c-4) crospovidone is used not only as a disintegrating agent but also as a binder, a diluent, or another additive.

Other Ingredients

Solid Preparation D may contain other ingredients for use in pharmaceutical solid preparations, in addition to the Components (a), (b) and (c-4). Examples of the ingredients include diluents, binders, pH adjusters, absorption enhancers, lubricants, colorant flavoring agents, or perfumes. The contents of these additional ingredients fall within the range not to impair the effect of the present invention.

Solid Preparation D containing (a) benzoazepine compound, the (b) hydroxypropylcellulose containing a hydroxy propoxyl group in an amount of 50% or greater, and the (c-4) crospovidone may be in the form of a powder, granules, tablet, pill, or capsule. Among these, the present invention prefers the form of a powder, granules, capsules, or tablet in view of easy preparation and dose. Tablets are particularly preferable.

Production Method for Solid Preparation D

Solid Preparation D is prepared in the same manner as Solid Preparation A, except that crospovidone is used instead of low substituted hydroxypropylcellulose.

Each unit of Solid Preparations A to D of the present invention in the dosage form preferably contains the (a) benzoazepine compound as an active ingredient in an amount of about 0.1 to 120 mg, preferably about 1 to 90 mg, and more preferably about 5 to 60 mg.

The doses of Solid Preparations A to D are determined depending on the usage, the patient's condition including age and sex, the degree of disease, etc. Generally, the amount of the (a) benzoazepine compound as an active ingredient per day is about 0.02 to 2 mg per kg of the patient's weight.

Effect of the Invention

Pharmaceutical solid preparation of the present invention shows superior disintegration properties and excellent solubility, leading to sufficient absorbability of active ingredients in the gastrointestinal tract.

Particularly, Solid Preparation A according to the present invention ensures far superior disintegration properties and excellent solubility, leading to sufficient absorbability of active ingredients in the gastrointestinal tract.

Further, in the tablet form, Solid Preparation A of the present invention ensures uniform disintegration properties of the products, thereby reducing variation in disintegration time among the products. Consequently, Solid Preparation A is expected to exhibit the best invariable pharmacological effect and is thereby the most preferable.

The method according to the present invention produces a pharmaceutical solid preparation with these advantageous characteristics.

BEST MODE FOR CARRYING OUT THE INVENTION

The present invention is more specifically described below in reference to the Reference Examples, Examples, Comparative Examples and Experiment Examples; however, the present invention is not limited to those examples.

Reference Example 1 (Preparation of Amorphous Powder)

100 g of 7-chloro-5-hydroxy-1-[2-methyl-4-(2-methyl benzoylamino)benzoyl]-2,3,4,5-tetrahydro-1H-benzo-azepine ("main ingredient", hereinafter) and 50 g of hydroxypropylcellulose (HPC-SL; Nippon Soda Co. Ltd.) containing 53 to 78 wt. % of hydroxy propoxyl group was dissolved in a mixed solution of 1,390 g of dichloromethane and 350 g of ethanol. The solution was treated with an ODT-8 spray drier (Ohkawara Kakohki Co., Ltd.), and then immediately dried with an LCV-232 vacuum dryer (Tabai Espec Corporation), to prepare an amorphous powder.

Reference Example 2 (Preparation of Granulation Substance)

135 g of the amorphous powder, 222 g of lactose monohydrate, 60 g of corn starch, and 60 g of crystalline cellulose were mixed, and the mixture was placed in a Multiplex MP-01 stirring fluidized-bed granulation drier (Powrex Corporation). Fluidizing-bed granulation was carried out with 240 g of a 5 w/v % aqueous solution of hydroxypropylcellulose containing a hydroxy propoxyl group in an amount of 53 to 78 wt. % (HPC-L; Nippon Soda Co., Ltd.), followed by drying. A granulation substance was thus obtained.

In the Examples and Comparative Examples below, the following products were used as Component (c).

Component (c)
Low substituted hydroxypropylcellulose (an average particle diameter of 45 to 65 μm, and a 90% cumulative particle diameter of 150 to 200 μm; content of hydroxy propoxyl group=10.0 to 12.9 wt. %) (LH-11; Shin-Etsu Chemical Co., Ltd.)
Low substituted hydroxypropylcellulose (an average particle diameter of 35 to 55 μm, and a 90% cumulative particle diameter of 100 to 150 μm; content of hydroxy propoxyl group=10.0 to 12.9 wt. %) (LH-21; Shin-Etsu Chemical Co. Ltd.)
Low substituted hydroxypropylcellulose (an average particle diameter of 17 to 23 μm, and a 90% cumulative particle diameter of 40 to 100 μm; content of hydroxy propoxyl group=10.0 to 12.9 wt. %) (LH-31; Shin-Etsu Chemical Co. Ltd.)
Low substituted hydroxypropylcellulose (an average particle diameter of 45 to 65 μm, and a 90% cumulative particle diameter of 100 to 150 μm; content of hydroxy propoxyl group=10.0 to 12.9 wt. %) (LH-B1; Shin-Etsu Chemical Co. Ltd.)
Carmellose ((carboxymethylcellulose) NS-300; Nichirin Chemical Industries Ltd.)
Sodium carboxy methyl starch (Primojel; DMV; After a screening with a 63 μm sieve, 5% or less of the particles remain on the sieve)
Partly pregelatinized starch (PCS PC-10; Asahi Kasei Chemicals; an average particle diameter of 70 μm, not more than 3 wt. % water soluble content)
Crospovidone (Polyplasdone XL; ISP; an average particle diameter of 75 μm)
Carmellose calcium ((carboxymethylcellulose calcium) ECG-505; Nichirin Chemical Industries, Ltd.)
Crosscarmellose sodium ((crosscarboxymethylcellulose sodium) Ac-Di-Sol; FMC International)

Example 1

24.5 g of the granulation substance prepared in the above-mentioned Reference Example 2, 0.3 g of LH-11, and 0.3 g of magnesium stearate were mixed. Using an Autograph AG-I Universal Testing Instruments (Shimadzu Corporation), a flat tablet (6 mm in diameter) about 84 mg in weight, containing 15 mg of the main ingredient, was produced under a compression speed of 6 kN, with a compression rate of 20 mm/min.

The content of LH-11 in the flat tablet was 1.2 wt. %.

Example 2

24.5 g of the granulation substance prepared in the above-mentioned Reference Example 2, 1.4 g of LH-11, and 0.3 g of magnesium stearate were mixed. A flat tablet about 87 mg in weight, containing 15 mg of the main ingredient, was produced in the same manner as Example 1.

The content of LH-11 in the flat tablet was 5.2 wt. %.

Example 3

24.5 g of the granulation substance prepared in the above-mentioned Reference Example 2, 2.9 g of LH-11, and 0.4 g of magnesium stearate were mixed. A flat tablet about 92 mg in weight, containing 15 mg of the main ingredient, was produced in the same manner as Example 1.

The content of LH-11 in the flat tablet was 10.3 wt. %.

Example 4

24.5 g of the granulation substance prepared in the above-mentioned Reference Example 2, 4.4 g of LH-11, and 0.3 g of magnesium stearate were mixed. A flat tablet about 97 mg in weight, containing 15 mg of the main ingredient, was produced in the same manner as Example 1.

The content of LH-11 in the flat tablet was 14.9 wt. %.

Example 5

8.2 g of the granulation substance prepared in the above-mentioned Reference Example 2, 0.5 g of LH-21, and 0.1 g of magnesium stearate were mixed. A flat tablet about 87 mg in weight, containing 15 mg of the main ingredient, was produced in the same manner as Example 1.

The content of LH-21 in the flat tablet was 5.2 wt. %.

Example 6

8.2 g of the granulation substance prepared in the above-mentioned Reference Example 2, 0.5 g of LH-B1, and 0.1 g of magnesium stearate were mixed. A flat tablet about 87 mg in weight, containing 15 mg of the main ingredient, was produced in the same manner of Example 1.

The content of LH-B1 in the flat tablet was 5.2 wt. %.

Comparative Example 1

24.5 g of the granulation substance prepared in the above-mentioned Reference Example 2, and 0.3 g of magnesium stearate were mixed. A flat tablet about 83 mg in weight, containing 15 mg of the main ingredient, was produced in the same manner as Example 1.

Comparative Example 2

8.2 g of the granulation substance prepared in the above-mentioned Reference Example 2, 0.1 g of LH-31, and 0.1 g of magnesium stearate were mixed. A flat tablet about 84 mg in weight, containing 15 mg of the main ingredient, was produced in the same manner as Example 1.

The content of LH-31 in the flat tablet was 1.2 wt. %.

Comparative Example 3

8.2 g of the granulation substance prepared in the above-mentioned Reference Example 2, 0.5 g of LH-31, and 0.1 g of magnesium stearate were mixed. A flat tablet about 87 mg in weight, containing 15 mg of the main ingredient, was produced in the same manner as Example 1.

The content of LH-31 in the flat tablet was 5.2 wt. %.

Comparative Example 4

24.5 g of the granulation substance prepared in the above-mentioned Reference Example 2, 0.3 g of Ac-Di-Sol, and 0.3 g of magnesium stearate were mixed. A flat tablet about 84 mg in weight, containing 15 mg of the main ingredient, was produced in the same manner as Example 1.

The content of Ac-Di-Sol in the flat tablet was 1.2 wt. %.

Comparative Example 5

24.5 g of the granulation substance prepared in the above-mentioned Reference Example 2, 1.3 g of Ac-Di-Sol, and 0.3 g of magnesium stearate were mixed. A flat tablet about 87 mg in weight, containing 15 mg of the main ingredient, was produced in the same manner as Example 1.

The content of Ac-Di-Sol in the flat tablet was 5.2 wt. %.

Comparative Example 6

24.5 g of the granulation substance prepared in the above-mentioned Reference Example 2, 2.9 g of Ac-Di-Sol, and 0.3 g of magnesium stearate were mixed. A flat tablet about 92 mg in weight, containing 15 mg of the main ingredient, was produced in the same manner as Example 1.

The content of Ac-Di-Sol in the flat tablet was 10.3 wt. %.

Comparative Example 7

24.5 g of the granulation substance prepared in the above-mentioned Reference Example 2, 4.4 g of Ac-Di-Sol, and 0.3 g of magnesium stearate were mixed. A flat tablet about 97 mg in weight, containing 15 mg of the main ingredient, was produced in the same manner as Example 1.

The content of Ac-Di-Sol in the flat tablet was 14.9 wt. %.

Comparative Example 8

24.5 g of the granulation substance prepared in the above-mentioned Reference Example 2, 0.3 g of ECG-505, and 0.3 g of magnesium stearate were mixed. A flat tablet about 84 mg in weight, containing 15 mg of the main ingredient, was produced in the same manner as Example 1.

The content of ECG-505 in the flat tablet was 1.2 wt. %.

Comparative Example 9

24.5 g of the granulation substance prepared in the above-mentioned Reference Example 2, 1.4 g of ECG-505, and 0.3 g of magnesium stearate were mixed. A flat tablet about 87 mg in weight, containing 15 mg of the main ingredient, was produced in the same manner as Example 1.

The content of ECG-505 in the flat tablet was 5.2 wt. %.

Comparative Example 10

24.5 g of the granulation substance prepared in the above-mentioned Reference Example 2, 2.9 g of ECG-505, and 0.3 g of magnesium stearate were mixed. A flat tablet about 92 mg in weight, containing 15 mg of the main ingredient, was produced in the same manner as Example 1.

The content of ECG-505 in the flat tablet was 10.3 wt. %.

Comparative Example 11

24.5 g of the granulation substance prepared in the above-mentioned Reference Example 2, 4.4 g of ECG-505, and 0.3 g of magnesium stearate are mixed. A flat tablet about 97 mg in weight, containing 15 mg of the main ingredient, was produced in the same manner as Example 1.

The content of ECG-505 in the flat tablet was 14.9 wt. %.

Experiment Example 1

Using six tablets each, the respective tablets prepared in Examples 1 to 6 and Comparative Examples 1 to 11 were examined for their disintegration properties according to a disintegration test method disclosed in Japanese Pharmacopoeia (test fluid: water, no disk).

Table 1 shows the results of the disintegration test for Examples 1 to 6 and Comparative Examples 1 to 11.

TABLE 1

| Flat Tablet | Disintegration Time (Second, Average ± standard Deviation) |
|---|---|
| Example 1 (LH-11, 1.2%) | 70.8 ± 5.8 |
| Example 2 (LH-11, 5.2%) | 63.7 ± 3.9 |
| Example 3 (LH-11, 10.3%) | 52.8 ± 2.4 |
| Example 4 (LH-11, 14.9%) | 60.5 ± 2.0 |
| Example 5 (LH-21, 5.2%) | 79.8 ± 10.7 |
| Example 6 (LH-B1, 5.2%) | 75.5 ± 1.9 |
| Comparative Example 1 (No Disintegrating Agent) | 95.8 ± 6.1 |
| Comparative Example 2 (LH-31, 1.2%) | 104.7 ± 6.2 |
| Comparative Example 3 (LH-31, 5.2%) | 130.3 ± 37.4 |
| Comparative Example 4 (Ac-Di-Sol, 1.2%) | 92.3 ± 3.0 |
| Comparative Example 5 (Ac-Di-Sol, 5.2%) | 161.3 ± 12.0 |
| Comparative Example 6 (Ac-Di-Sol, 10.3%) | 163.8 ± 3.5 |
| Comparative Example 7 (Ac-Di-Sol, 14.9%) | 188.0 ± 3.8 |
| Comparative Example 8 (ECG-505, 1.2%) | 85.5 ± 3.9 |
| Comparative Example 9 (ECG-505, 5.2%) | 100.5 ± 5.1 |
| Comparative Example 10 (ECG-505, 10.3%) | 130.3 ± 4.5 |
| Comparative Example 11 (ECG-505, 14.9%) | 170.0 ± 5.1 |

Table 1 revealed the following.

For the tablets of Comparative Examples 2 and 3 that use LH-31 (low substituted hydroxypropylcellulose (an average particle diameter of 17 to 23 μm, and a 90% cumulative particle diameter of 40 to 100 μm), the disintegration time was longer than Comparative Example 1 not containing a disintegrating agent.

The disintegration time in the tablet of Comparative Example 4 containing 1.2 wt. % of Ac-Di-Sol (cross carmellose sodium) and in the tablet of Comparative Example 8 containing of 1.2 wt. % of ECG-505 (carmellose sodium) was slightly shorter than that in the tablet of Comparative Example 1 not containing any disintegrating agents. However, by increasing the proportions of Ac-Di-Sol and ECG-505 in the tablets to 5.2 wt. %, 10.3 wt. %, and 14.9 wt. % (Comparative Examples 5 to 7 and Comparative Examples 9 to 11), the disintegration time lengthened remarkably.

Although Ac-Di-Sol used in Comparative Examples 4 to 7 and ECG-505 used in Comparative Examples 8 to 11 are known as super disintegration agents, the tablets using these disintegration agents instead of the disintegration agents used for the present invention turned out to exhibit insufficient disintegration properties. Moreover, as its amount increased, the disintegration properties lowered significantly.

In contrast, as shown in Table 1, the disintegration time was significantly short in Examples 1 to 4 using LH-11 as a disintegrating agent, compared with Comparative Examples 1 to 11, and desirable disintegration properties were obtained.

Additionally, in the solid preparation of Example 5 which uses LH-21 as a disintegrating agent, the disintegration time was shorter than Comparative Example 1 not containing any disintegrating agent, and desirable disintegration properties were obtained.

Further, in the solid preparation of Example 6 which uses LH-B1 as disintegrating agent, the disintegration time was shorter than Comparative Example 1 not containing any disintegrating agents. Desirable disintegration properties were thus obtained.

Experiment Example 2

Table 2 shows the average value and variation in disintegration time among the six solid samples (No. 1 to 6) for each of Examples 2, 5, and 6 and Comparative Example 3, which were measured in the above-mentioned Experiment Example 1.

TABLE 2

| | Solid Preparation No. | Example 2 | Example 5 | Example 6 | Comparative Example 3 |
|---|---|---|---|---|---|
| Disintegration Time (Seconds) | 1 | 58 | 70 | 73 | 106 |
| | 2 | 60 | 72 | 74 | 107 |
| | 3 | 64 | 73 | 75 | 112 |
| | 4 | 66 | 80 | 76 | 121 |
| | 5 | 66 | 86 | 77 | 132 |
| | 6 | 68 | 98 | 78 | 204 |
| Average Disintegration Time (Seconds) | | 63.7 | 79.8 | 75.5 | 130.3 |
| Variation (Seconds) | | 3.9 | 10.7 | 1.9 | 37.4 |

As shown in Table 2, the variation in disintegration time in Example 2 using LH-11 as a disintegrating agent was 3.9 seconds; the variation in disintegration time in Example 5 using LH-21 was 10.7 seconds; and the variation in disintegration time in Example 6 using LH-B1 was 1.9 seconds. That is, the variation in disintegration time was small for the tablets of all Examples 2, 5, and 6; more specifically, the tablets of these Examples ensure a uniform pharmacologic effect.

Meanwhile, the variation in disintegration time in Comparative Example 3 using LH-31 was 37.4 seconds, which is very large.

Example 7

8.2 g of the granulation substance prepared in the above-mentioned Reference Example 2, 0.5 g of NS-300, and 0.1 g of magnesium stearate were mixed. A flat tablet about 87 mg in weight, containing 15 mg of the main ingredient, was produced in the same manner as Example 1.

The content of NS-300 in the flat tablet was 5.2 wt. %.

Example 8

8.2 g of the granulation substance prepared in the above-mentioned Reference Example 2, 1.0 g of NS-300, and 0.1 g of magnesium stearate were mixed. A flat tablet about 92 mg in weight, containing 15 mg of the main ingredient, was produced in the same manner as Example 1.

The content of NS-300 in the flat tablet was 10.3 wt. %.

Experiment Example 3

A disintegration test was conducted for each of the six solid samples in Examples 7 and 8, using a disintegration test method according to Japanese Pharmacopoeia (test fluid: water, no disk).

Table 3 shows the results of the disintegration test for Examples 7 and 8.

TABLE 3

|  | Disintegration Time (Seconds, Average ± standard Deviation) |
|---|---|
| Example 7 (NS-300, 5.2%) | 88.8 ± 7.0 |
| Example 8 (NS-300, 10.3%) | 55.2 ± 15.1 |

Table 3 revealed the following.

In the solid preparations of Examples 7 and 8, using NS-300 as a disintegrating agent, their disintegration times were shorter than that of Comparative Example 1 (shown in Table 1) not containing any disintegrating agents, and desirable disintegration properties were obtained.

Particularly, the disintegration time of Example 8 using 10.3 wt. % of NS-300 in each table was significantly shorter than that of Comparative Examples 1 to 11. The disintegration properties of Example 8 were thus excellent.

Example 9

8.2 g of the granulation substance prepared in the above-mentioned Reference Example 2, 0.1 g of Primojel, and 0.1 g of magnesium stearate were mixed. A flat tablet about 84 mg in weight, containing 15 mg of the main ingredient, was produced in the same manner as Example 1.

The content of Primojel in the flat tablet was 1.2 wt. %.

Example 10

8.2 g of the granulation substance prepared in the above-mentioned Reference Example 2, 0.5 g of Primojel, and 0.1 g of magnesium stearate were mixed. A flat tablet about 87 mg in weight, containing 15 mg of the main ingredient, was produced in the same manner as Example 1.

The content of Primojel in the flat tablet was 5.2 wt. %.

Example 11

8.2 g of the granulation substance prepared in the above-mentioned Reference Example 2, 1.0 g of Primojel, and 0.1 g of magnesium stearate were mixed. A flat tablet about 92 mg in weight, containing 15 mg of the main ingredient, was produced in the same manner as Example 1.

The content of Primojel in the flat tablet was 10.3 wt. %.

Example 12

8.2 g of the granulation substance prepared in the above-mentioned Reference Example 2, 0.5 g of PCS PC-10, and 0.1 g of magnesium stearate were mixed. A flat tablet about 87 mg in weight, containing 15 mg of the main ingredient, was produced in the same manner as Example 1.

The content of PCS PC-10 in the flat tablet was 5.2 wt. %.

Example 13

8.2 g of the granulation substance prepared in the above-mentioned Reference Example 2, 1.0 g of PCS PC-10, and 0.1 g of magnesium stearate were mixed. A flat tablet about 92 mg in weight, containing 15 mg of the main ingredient, was produced in the same manner as Example 1.

The content of PCS PC-10 in the flat tablet was 10.3 wt. %.

Experiment Example 4

A disintegration test was conducted for each of the six solid samples in Examples 9 to 13, using a disintegration test method according to Japanese Pharmacopoeia (test fluid: water, no disk).

Table 4 shows the results of the disintegration test for Examples 9 to 13.

TABLE 4

|  | Disintegration Time (Seconds, Average ± standard Deviation) |
|---|---|
| Example 9 (Primojel, 1.2%) | 58.8 ± 7.4 |
| Example 10 (Primojel, 5.2%) | 65.2 ± 4.2 |
| Example 11 (Primojel, 10.3%) | 72.2 ± 7.4 |
| Example 12 (PCS PC-10, 5.2%) | 87.2 ± 5.3 |
| Example 13 (PCS PC-10, 10.3%) | 92.5 ± 2.9 |

Table 4 revealed the following.

In the solid preparations of Examples 9 to 11 using Primojel (sodium carboxy methyl starch) as a disintegrating agent, the disintegration time was shorter than that of Comparative Example 1 not containing any disintegrating agents, and desirable disintegration properties were obtained.

Particularly, the disintegration time was significantly short in Example 9 using 1.2 wt. % of Primojel as a disintegrating agent, compared with Comparative Examples 1 to 11. The disintegration properties of Example 9 were thus excellent.

Additionally, in the solid preparations of Examples 12 and using PCS PC-10 (partly pregelatinized starch) as a disintegrating agent, the disintegration time was shorter than Comparative Example 1 not containing a disintegrating agent, and desirable disintegration properties were obtained.

Example 14

8.2 g of the granulation substance prepared in the above-mentioned Reference Example 2, 0.1 g of Polyplasdone XL, and 0.1 g of magnesium stearate were mixed. A flat tablet about 84 mg in weight, containing 15 mg of the main ingredient, was produced in the same manner as Example 1.

The content of Polyplasdone XL in the flat tablet was 1.2 wt. %.

Example 15

8.2 g of the granulation substance prepared in the above-mentioned Reference Example 2, 0.5 g of Polyplasdone XL, and 0.1 g of magnesium stearate were mixed. A flat tablet about 87 mg in weight, containing 15 mg of the main ingredient, was produced in the same manner as Example 1.

The content of Polyplasdone XL in the flat tablet was 5.2 wt. %.

Example 16

8.2 g of the granulation substance prepared in the above-mentioned Reference Example 2, 1.0 g of Polyplasdone XL, and 0.1 g of magnesium stearate were mixed. A flat tablet about 92 mg in weight, containing 15 mg of the main ingredient, was produced in the same manner as Example 1.

The content of Polyplasdone XL in the flat tablet was 10.3 wt. %.

Experiment Example 5

A disintegration test was conducted for each of the six solid samples in Examples 14 to 16, using a disintegration test method according to Japanese Pharmacopeia (test fluid: water, no disk).

Table 5 shows the results of the disintegration test for Examples 14 to 16.

TABLE 5

|  | Disintegration Time (Seconds, Average ± standard Deviation) |
|---|---|
| Example 14 (Polyplasdone XL, 1.2%) | 80.5 ± 19.9 |
| Example 15 (Polyplasdone XL, 5.2%) | 73.5 ± 6.6 |
| Example 16 (Polyplasdone XL, 10.3%) | 53.8 ± 3.4 |

Table 5 revealed the following.

In the solid preparations of Examples 14 to 16 using Polyplasdone XL (crospovidone) as a disintegrating agent, the disintegration time was shorter than that of Comparative Examples 1 to 11, and desirable disintegration properties were obtained.

Particularly, the disintegration time was significantly short in Example 16 using the solid preparation containing 10.3 wt. % of Polyplasdone XL. The disintegration properties of Example 16 were thus excellent.

Example 17

270 g of the amorphous powder obtained in Reference Example 1, 50.5 g of lactose monohydrate, 60 g of corn starch, and 60 g of crystalline cellulose were mixed, and the mixture was placed in a Multiplex MP-01 stirring fluidized-bed granulation drier (Powrex Corporation). Fluidizing-bed granulation was carried out with 240 g of a 5 w/v % aqueous solution of hydroxypropylcellulose containing a hydroxy propoxyl group in an amount of 53 to 78 wt. %, followed by drying. A granulation substance was thus obtained in the same manner as Reference Example 2. The obtained granulation substance was mixed with 27 g of LH-11, 0.48 g of FDC blue No. 2 aluminum lake, and 6 g of magnesium stearate to prepare granules for tablets. With the obtained granules, flat tablets were produced with a Rotary Tabletting Machine 12HUK-AWC (product of Kikusui Seisakusho Ltd.), at 40 rpm and under a compression force at 900 kg. Each tablet was about 162 mg in weight, 8 mm in diameter, and contains 60 mg of a main ingredient. The content of LH-11 in each tablet was 5.6 wt. %.

Example 18

112.5 g of the amorphous powder obtained in Reference Example 1, 184.6 g of lactose monohydrate, 50 g of corn starch, and 50 g of crystalline cellulose were mixed, and the mixture was placed in a Multiplex MP-01 stirring fluidized-bed granulation drier (Powrex Corporation). Fluidizing-bed granulation was carried out with 200 g of a 5 w/v % aqueous solution of hydroxypropylcellulose containing a hydroxy propoxyl group in an amount of 53 to 78 wt. %, followed by drying. A granulation substance was thus obtained in the same manner as Reference Example 2. The obtained granulation substance was mixed with 22.5 g of LH-11, 0.43 g of FDC blue No. 2 aluminum lake, and 5 g of magnesium stearate to prepare granules for tablets. With the obtained granules, flat tablets were produced with a Rotary-Tabletting Machine 12HUK-AWC (product of Kikusui Seisakusho Ltd.), at 40 rpm and under a compression force at 900 kg. Each tablet was about 174 mg in weight, 8 mm in diameter, and contains 30 mg of a main ingredient. The content of LH-11 in each tablet was 5.2 wt. %.

Example 19

With the granules obtained in Example 18, flat tablets were produced with a Rotary Tabletting Machine 12HUK-AWC (product of Kikusui Seisakusho Ltd.), at 40 rpm and under a compression force at 900 kg. Each tablet was about 87 mg in weight, 6 mm in diameter, and contains 15 mg of a main ingredient. The content of LH-11 in each tablet was 5.2 wt. %.

Example 20

56.3 g of the amorphous powder obtained in Reference Example 1, 255.8 g of lactose monohydrate, 50 g of corn starch, and 50 g of crystalline cellulose were mixed, and the mixture was placed in a Multiplex MP-01 stirring fluidized-bed granulation drier (Powrex Corporation). Fluidizing-bed granulation was carried out with 200 g of a 5 w/v % aqueous solution of hydroxypropylcellulose containing a hydroxy propoxyl group in an amount of 53 to 78 wt. %, followed by drying. A granulation substance was thus obtained in the same manner as Reference Example 2. The obtained granulation substance was mixed with 22.5 g of LH-11, 0.45 g of FDC blue No. 2 aluminum lake, and 5 g of magnesium stearate to prepare granules for tablets. With the obtained granules, flat tablets were produced with a Rotary Tabletting Machine 12HUK-AWC (product of Kikusui Seisakusho Ltd.), at 50 rpm and under a compression force at 1000 kg. Each tablet was about 180 mg in weight, 8 mm in diameter, and contains 15 mg of a main ingredient. The content of LH-11 in each tablet was 5.0 wt. %.

Example 21

33.75 g of the amorphous powder obtained in Reference Example 1, 350.25 g of lactose monohydrate, 60 g of corn starch, and 60 g of crystalline cellulose were mixed, and the mixture was placed in a Multiplex MP-01 stirring fluidized-bed granulation drier (Powrex Corporation). Fluidizing-bed granulation was carried out with 240 g of a 5 w/v % aqueous solution of hydroxypropylcellulose containing a hydroxy propoxyl group in an amount of 53 to 78 wt. %, followed by drying. A granulation substance was thus obtained in the same manner as Reference Example 2. The obtained granulation substance was mixed with 27 g of LH-11, and 6 g of magnesium stearate to prepare granules for tablets. With the obtained granules, flat tablets were produced with a Rotary Tabletting Machine 12HUK-AWC (product of Kikusui Seisakusho Ltd.), at 50 rpm and under a compression force at 1000 kg. Each tablet was about 183 mg in weight, 8 mm in diameter, and contains 7.5 mg of a main ingredient. The content of LH-11 in each tablet was 4.9 wt. %.

INDUSTRIAL APPLICABILITY

The pharmaceutical solid preparation of the present invention contains (a) benzoazepine compound, (b) hydroxypropylcellulose containing a hydroxy propoxyl group in an amount of 50% or greater, and a disintegrating agent, which is either (c-1) low substituted hydroxypropylcellulose, (c-2) carmellose, (c-3) sodium carboxy methyl starch or (c-4) crospovidone. With this composition, the pharmaceutical solid preparation of the present invention ensures superior disintegration properties and excellent solubility, leading to sufficient absorbability of the active ingredient through the gastrointestinal tract. The pharmaceutical solid preparation of the present invention therefore serves many uses in the medical field. The production method of the present invention provides the pharmaceutical solid preparation with such superior characteristics.

The invention claimed is:

1. A pharmaceutical solid preparation obtained by a method, comprising:
   Step 1 of producing amorphous composites consisting of (a) 7-chloro-5-hydroxy-1-[2-methyl-4-(2-methylbenzoylamino)benzoyl]-2,3,4,5-tetrahydro-1H-benzoazepine and/or salt thereof, and (b) hydroxypropylcellulose containing a hydroxypropoxyl group in an amount of 50% or greater;
   Step A of processing a mixture of (i) the amorphous composites obtained in Step 1, (ii) crystalline cellulose, and (iii) corn starch and/or lactose into granules using a granulation method;
   Step 2 of mixing the granules obtained in Step A with (c-1) low substituted hydroxypropylcellulose, to obtain a mixture, wherein the low substituted hydroxypropylcellulose is cellulose containing a hydroxy propoxyl group in an amount of about 10 to 13%, has an average particle diameter of 45 to 65 µm, and has a 90% cumulative particle diameter of 150 to 200 µm, and the component (c-1) directly contacts at least some of the amorphous composites; and
   Step 3 of processing the mixture obtained in Step 2 into a solid preparation,
   wherein the content of the component (c-1) is 1 to 15 wt % of the solid preparation.

2. The pharmaceutical solid preparation according to claim 1, wherein the pharmaceutical solid preparation is a form of tablet.

3. The pharmaceutical solid preparation according to claim 2, wherein Step 3 includes coating the tablet with an enteric film or a sustained-release film to modify a drug release in the gastrointestinal tract.

4. The pharmaceutical solid preparation according to claim 1, wherein the content of (a) the 7-chloro-5-hydroxy-1-[2-methyl-4-(2-methylbenzoylamino)benzoyl]-2,3,4,5-tetrahydro-1H-benzoazepine and/or salt thereof is 0.01 to 95 wt % of the solid preparation.

5. The pharmaceutical solid preparation according to claim 1, wherein the content of (b) the hydroxypropylcellulose containing the hydroxypropoxyl group in the amount of 50% or greater is 0.01 to 2 times that of the content of (a) the 7-chloro-5-hydroxy-1-[2-methyl-4-(2-methylbenzoylamino)benzoyl]-2,3,4,5-tetrahydro-1H-benzoazepine and/or salt thereof in the solid preparation.

6. The pharmaceutical solid preparation according to claim 1, wherein the content of the component (c-1) is 3 to 12 wt % of the solid preparation.

* * * * *